(12) United States Patent
Holly et al.

(10) Patent No.: US 7,473,898 B2
(45) Date of Patent: Jan. 6, 2009

(54) CRYOGENIC TERAHERTZ SPECTROSCOPY

(75) Inventors: Sandor Holly, Woodland Hills, CA (US); Nicholas Koumvakalis, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 135 days.

(21) Appl. No.: 11/436,715

(22) Filed: May 17, 2006

(65) Prior Publication Data

US 2007/0267575 A1   Nov. 22, 2007

(51) Int. Cl.
*G01J 5/02* (2006.01)
(52) U.S. Cl. .............. 250/343; 250/339.13; 250/339.04
(58) Field of Classification Search ................ 250/343, 250/339.13, 339.03, 339.04
See application file for complete search history.

(56) References Cited

U.S. PATENT DOCUMENTS

| | | | | |
|---|---|---|---|---|
| 4,264,814 | A * | 4/1981 | Freund et al. | 250/304 |
| 4,600,559 | A * | 7/1986 | Hiatt | 422/89 |
| 5,939,721 | A * | 8/1999 | Jacobsen et al. | 250/330 |
| 6,944,486 | B2 * | 9/2005 | Braig et al. | 600/310 |
| 2006/0202123 | A1 * | 9/2006 | Vuillermoz et al. | 250/343 |

OTHER PUBLICATIONS

Maier, W. B., Freund, S. M., Holland, R. F. & Beattie, W. H. J. chem. Phys. 69, 1961 (1978).*
J. T. Kindt and C. A. Schmuttenmaer. Far-infrared dielectric properties of polar liquids probed by femtosecond THz pulse spectroscopy. Journal of Physical Chemistry, 100:10373-10379, 1996.*

* cited by examiner

*Primary Examiner*—David P Porta
*Assistant Examiner*—Jessica L Eley
(74) *Attorney, Agent, or Firm*—Macpherson Kwok Chen & Heid LLP; Norman Carte

(57) ABSTRACT

A terahertz spectroscopy system includes a source of terahertz radiation, a detector of terahertz radiation, a source of sample gas, and a sample cell that can be cooled to cryogenic temperatures. The sample cell may be configured to receive the sample gas, received terahertz radiation from the source of terahertz radiation, provide the terahertz radiation to the detector after the terahertz radiation has passed through the sample gas, and facilitate cryogenic cooling thereof. The sample cell may be cryogenically cooled to freeze the sample gas and subsequently warmed either continuously or in steps in temperature so that individual components or groups of components of the sample gas may evaporate and thus have absorption spectra formed therefor. Enhanced resolution of absorption spectra is provided when a gas sample contains a large number of components of different gases.

26 Claims, 3 Drawing Sheets

CRYOGENIC TERAHERTZ SPECTROSCOPY

TECHNICAL FIELD

The present invention relates generally to spectroscopy and, more particularly, to the use of a cryogenic sample cell for enhancing the performance of terahertz spectroscopy, particularly on complex gas samples.

BACKGROUND

Time Domain Terahertz Spectroscopy (TDTS) of gases is known. Time Domain Terahertz Spectroscopy utilizes substantially the same procedure used in the more traditional Time Domain spectroscopy (TDS), which is performed at optical frequencies.

In either instance (TDTS or TDS), the frequency of radiation from a narrowband source is swept through a given frequency range. In general practice the radiation (infrared, visible, ultraviolet, etc) is transmitted through a sample of the material to be analyzed. The sample is typically contained within a sample cell.

An absorption spectrum is measured using radiation that has passed through the sample. A photodetector or another type of sensor that is sensitive to frequencies within the frequency range being scanned is used to measure the absorption spectra.

High resolution spectroscopy requires the use of a tunable radiation source. The radiation source must have a very narrow line width in order to provide the desired resolution. The maximum scan rate that may be used depends upon characteristics (such as sensor bandwidth) of the detector used. However, the resolution of minute variations of absorption as a function of frequency may require that the scan rate be significantly reduced.

When a large number of different species of gases coexist in the sample, the required spectral resolution of the measuring instrument is greatly increased. Better spectral resolution is necessary in order to identify each species and relative strengths (partial pressures) thereof. This is true for the spectroscopic measurement of gases in the terahertz regime, as well as when using more conventional frequencies.

Key characteristic lines of the absorption spectra of gases with complex (large) molecules tend to lie in the far infrared (sub-millimeter wave) portion of the electromagnetic spectrum. Many such lines may be crowded into this portion of the electromagnet spectrum, making the resolution of individual lines difficult.

One problem associated with contemporary attempts at implementing Time Domain Terahertz Spectroscopy is that associated with obtaining high quality terahertz radiation sources. These sources need to have narrow line-widths, adequate power, and be rapidly tunable.

Further, sensitive and high speed terahertz detectors are difficult to obtain. Restrictions on weight, volume, and cost, as well as the desire for extremely high sensitivity (parts per trillion), increase the difficulty of obtaining suitable detectors. These problems are greatly exacerbated when there is a need to handle several hundred gas species that co-exist simultaneously in a single sample.

As a result, there is a need for a terahertz spectroscopy system suitable for analyzing samples containing many gas species. It would be beneficial if the system could use terahertz radiation sources and detectors having reduced resolution requirements. Further, the terahertz spectroscopy system needs to have desirable weight, volume, cost, and sensitivity.

SUMMARY

Systems and methods are disclosed herein to provide a sample cell for use in spectroscopy. The sample cell may be configured for cryogenic cooling thereof, so as to facilitate enhanced spectroscopy measurement resolution. Either the entire sample cell or a portion thereof may be cryogenically cooled.

In this manner, the resolution of the spectroscopy system may be enhanced without requiring enhancement of the resolution of the radiation source or the detector. Indeed, the resolution requirements of the source and that detector may be reduced.

For example, one or more cryogenic cooling conduits may be wrapped around the sample cell. The cryogenic cooling conduits can be in intimate contact with the sample cell. Alternatively, a cold finger or other cooled surface may be placed within the sample cell.

More particularly, the sample cell may comprise a sample chamber, a gas inlet port for introducing gas into the sample chamber, a gas outlet port for venting gas from the test chamber, a terahertz radiation input window for transmitting terahertz radiation into the sample chamber, a terahertz radiation output window for transmitting terahertz radiation out of the test chamber, and at least one cryogenic cooling/heating conduit configured to facilitate selective condensing of the gas.

Optionally, an electric heater or any other desired means may be used to warm the sample cell, and consequently the gas sample itself. Indeed, the gas sample may be warmed simply by discontinuing cryogenic cooling and thereby allowing the sample cell to return slowly to ambient temperature. Temperature monitoring inside of the test cell can be provided.

At least one surface within the sample cell may be configured such that gas condenses thereon when the sample cell is cooled and gas evaporates therefrom when the sample cell is warmed.

Optionally, one or more reflectors may be configured so as to increase a path length of terahertz radiation within the sample chamber. Any desired number of reflectors may be used to increase the path length of terahertz radiation. In this manner, enhanced exposure of the terahertz radiation to the sample gas is provided, so as to provide enhanced system sensitivity.

Moreover, a terahertz spectroscopy system may comprise a source of terahertz radiation, a detector of terahertz radiation, a source of sample gas, and a sample cell. The sample cell may be configured to receive the sample gas, receive terahertz radiation from the source of terahertz radiation, transmit the terahertz radiation to the detector after the terahertz radiation has passed through the sample gas, and provide means for accurately monitoring sample gas temperature so as to facilitate cryogenic cooling of the sample.

The source of terahertz radiation may comprises a variable, i.e., tunable, frequency source. The detector of the terahertz radiation may comprise a detector that is sensitive to a range of frequencies. The frequency range of the source and the detector will typically have substantially overlapping ranges, since the detector generally needs to detect frequencies provided by the source.

According to an embodiment of the present invention, a method of performing spectroscopy comprises flowing a sample gas into a sample cell, cooling the sample cell (or a portion thereof) so as to condense the sampled gas, warming the sample cell so as to cause component gases of the sample gas to evaporate at different well controlled temperatures, and performing spectroscopy upon the component gases.

The temperature of the sample cell may be increased in a series of discrete steps. Thus, spectroscopy may be performed upon the component gases of the sample so as to define a series of absorption spectra as different gas components vaporize.

More particularly, according to an embodiment of the present invention, a method for performing spectroscopy comprises defining a first absorption spectra, increasing a temperature of the sample, defining a second absorption spectra, and subtracting the first absorption spectra from the second absorption spectra so as to define a third absorption spectrum.

Because the spectra are separated, the resolution requirements of the spectroscopy system are reduced. Thus, a Time Domain Terahertz Spectroscopy (TDTS) system may use terahertz radiation sources and detectors having reduced resolution requirements.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
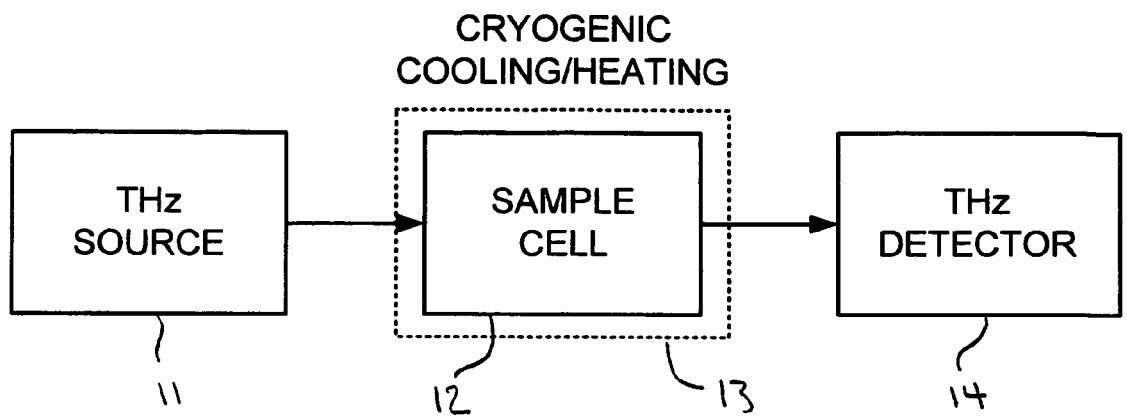
FIG. 1 shows a block diagram illustrating a cryogenic terahertz spectroscopy system in accordance with an exemplary embodiment of the present invention.

A gas sample may contain many, e.g., several hundred, different gases. According to one embodiment of the present invention, the terahertz absorption spectra of the various gases of a gas sample are separated in a manner that simplifies analysis thereof. That is, instead of all of the spectra being present during a single spectroscopic measurement, only a portion of the spectra are present during each measurement. This is accomplished by performing spectroscopic measurements upon the species or components of the gas sample one component or group of components at a time.

The spectroscopic measurements of the individual components or groups of components may be performed sequentially. In this manner, a single, comparatively complex spectrum is divided into a plurality of substantially less complex spectra. The less complex spectra may provide enhanced resolution and inherently easier recognition of individual gas species.

An embodiment of the present invention uses a cryogenically cooled gas sample cell. By controlling the temperature of the gas sample within the sample cell, the gases of the sample can be made to condense and then to selectively evaporate.

Thus, a spectroscopic measurement may be performed upon a selection of the gases according to a predetermined algorithm. That is, selected gases may be caused to boil off or evaporate by raising the temperature of a condensed sample above the freezing point of the selected gases. In this manner, the composite complex gas sample may be divided into its components or groups of components for enhanced spectroscopic measurements.

According to an embodiment of the present invention, a sample cell may be configured to be cryogenically cooled. Such cryogenic cooling may be effected by cooling the entire sample cell or by cooling a portion of the sample cell, e.g., an interior surface thereof. For example, cryogenic cooling coils may be wrapped around the cell, in intimate contact therewith, to effect such cooling. As a further example, a cold finger or cryogenic tube may extend into the sample cell and may either be in contact with a surface upon which sample gases condense or may define that surface itself. In either instance, the cold finger may define a condensation surface within the sample cell.

Initially, substantially all of the components of the gas sample may be condensed upon one or more surfaces of the sample chamber. The temperature may then be increased according to an accurately defined schedule. The schedule may depend upon the suspected components of the gas sample. Alternatively, the schedule may be generic, so as to contemplate the potential presence of a large number of components.

As the temperature of the condensed gas sample is increased, more of the components evaporate from the inside surface(s) into the volume of the test chamber (for example, into the inside volume of a Terahertz Fabry-Perot resonant cavity). An absorption spectrum is recorded. The absorption spectrum may be recorded digitally.

Each time that the gas sample's temperature is increased by a predetermined amount or step, $\Delta t$, some new gas components may evaporate within sample chamber and another absorption spectrum may be measured. The new gases that were added to any previously evaporated gases are known to belong to a group of gases having boiling points within the present $\Delta t$ temperature range. The temperature at which evaporation occurs may provide some additional information regarding the identification of the new gas components this information may be used in the analysis thereof.

The previously recorded absorption spectrum (which may comprise digital data) may be subtracted from this new absorption spectrum (which may also comprise digital data) and may be analyzed to determine new types of gas components that are now present. During each such temperature step, the new spectrum (the one determined by subtracting one spectrum from another) may be compared to the already known absorption spectra of those gases with boiling points within the current $\Delta t$ temperature interval. Thus, the gas components may be more readily identified since their boiling points are known. This procedure may be repeated until all of the gases are boiled off of the cryogenically cooled surface(s).

As the chamber temperature increases to the boiling points of $N_2$ and $O_2$, the noise floor of the absorption spectrum may increase substantially. However, much of this noise floor may be subtracted from the composite absorption spectrum. The absorption spectra of oxygen and nitrogen gases are well known.

Water vapor (from moisture in the air) will generally remain frozen until the top of the $\Delta t$ ramp is reached. Water vapor, if present, may interfere substantially with the absorption spectra of many gases especially since many gases may only be present in very small quantities, i.e., parts per trillion.

Referring now to FIG. 1, a cryogenic terahertz spectroscopy system may comprise a variable frequency, i.e., tunable, terahertz source 11 that provides terahertz radiation to a sample cell 12. The terahertz radiation may be swept in frequency so as to facilitate the measurement of an absorption spectrum for sample gas within sample cell 12. The terahertz radiation may be swept continuously, in discrete increments, or in any combination of continuously and incrementally.

Since the spectra are separated, a higher sweep rate may be used. The absorption bands are expected to be farther apart when the spectra are the result of the presence of one or just a few different gases. Thus, the need to enhance resolution by reducing the sweep rate may be substantially mitigated.

Any desired terahertz frequency range may be used. For example, to perform absorption spectra measurements on complex molecules, a frequency range of approximately 0.1 terahertz to approximately 10 terahertz may be used.

Terahertz source 11 may comprise a single tunable source, multiple tunable sources, or multiple discrete (non-tunable) sources. Terahertz source 11 may comprise any desired combination of tunable and discrete (non-tunable) sources.

Sample cell 12 may be cooled, such as via a cooling jacket, cooling tubes, or other means for cryogenically cooling thereof. For example a tube may be wrapped around sample cell 12 such that the tube is in intimate contact therewith. A cryogenic gas may then be caused to flow through the tube so as to cool sample cell 12 and cause the sample gas to condense upon a surface or surfaces thereof. As a further example, a cold finger may be made of diamond plates (or another material with superior thermal conductivity), with heater filaments (thin film, etc) deposited on at least one surface to facilitate accurate electronic control of its surface temperature. Materials with high thermal conductivity (such as diamond) can provide highly uniform temperature distribution over their entire surfaces.

Sample cell 12, i.e., more specifically, the cold finger surfaces, may also be warmed, such as in discrete Δt steps, so as to raise the temperature of the gas sample according to a predetermined schedule, as discussed above. Thus, a cryogenic cooling/heating system 13 may be used to precisely control and vary the temperature of sample cell 12.

Terahertz radiation from terahertz source 11 passes through sample cell 12, encountering the sample gas therein, and can be detected by a terahertz detector 14. As the frequency of terahertz source 11 is swept, terahertz detector 14 measures the terahertz radiation transmitted through sample cell 12 so as to facilitate the measurement of an absorption spectrum. This process may be repeated, at increasing temperatures of sample cell 12, so as to provide a plurality of absorption spectra having enhanced resolution.

Since the spectra are separated, and thus each spectrum is less complex, the resolution requirements of the terahertz source and the detector may be mitigated. Less resolution is required because there is less need to be able to separate closely spaced absorption bands in less complex spectra.

However, although the resolution requirements of the terahertz source and the detector may be mitigated, at least in some instances it may be desirable to maintain superior resolution capability. Thus, in such instances terahertz sources and detectors having higher resolution may be used. This may be beneficial, for example, in those instances where hundreds different gases are present in the sample chamber simultaneously.

Figure 2:
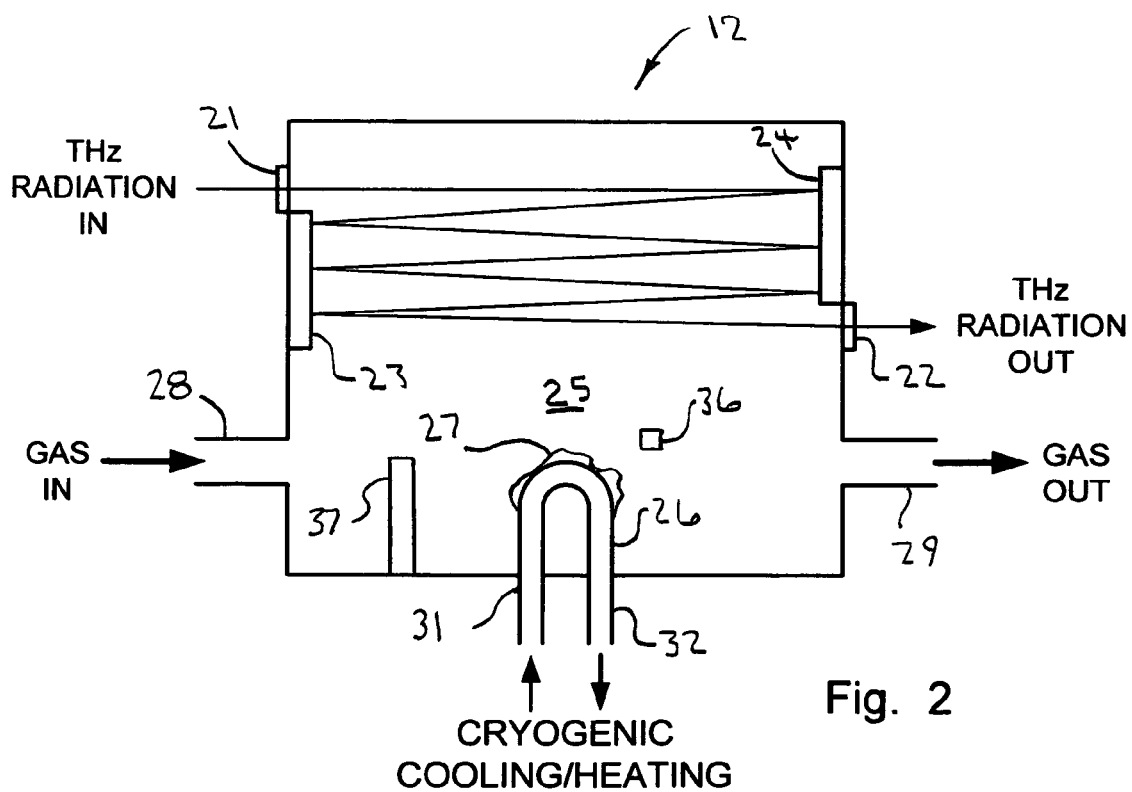
FIG. 2 shows a diagram illustrating an cryogenic sample cell in accordance with an exemplary embodiment of the present invention.

Referring now to FIG. 2, an embodiment of sample cell 12 that utilizes a cold finger 26 for cryogenic cooling of the sample gas is shown. An entrance window 21 admits terahertz radiation (such as from variable frequency terahertz source 11 of FIG. 1) into a chamber 25 of sample cell 12. Optionally, one or more mirrors or reflectors 23 and 24 may be used to increase the path length of the terahertz radiation within chamber 25, such as by reflecting the terahertz radiation back and forth repeatedly.

As those skilled in the art will appreciate, an increased path length effectively provides more of the sample gas for the terahertz radiation to travel through and be absorbed by, so as to enhance sensitivity of absorption spectra measurement. After traveling through chamber 25, the terahertz radiation exits sample cell 12 via exit window 22 and is incident upon a terahertz detector (such as terahertz detector 14 of FIG. 1).

Sample gas is provided to sample cell 12 via gas input port 28. Inside of chamber 25, the sample gas may be cooled by cold finger 26 such that it condenses thereon. Cryogenic fluid inlet 31 provides a cryogenic gas or cryogenic fluid to cold finger 26 and cryogenic gas or fluid outlet 32 facilitates gas or fluid flow from cold finger 26. Gas outlet port 29 facilitates the flow of sample gas out of chamber 25.

Alternatively, the entire sample cell 12 or any portion thereof may be cooled such that the sample gas condenses upon a surface thereof. Sample cell 12 may be cooled by any desired acceptable means.

Condensed sample gas 27 (such as that condensed upon cold finger 26) may subsequently be caused to evaporate one component or group of components at a time by slowing warming condensed sample gas 27. Condensed sample gas 27 may be warmed by varying the temperature of the fluid that flows through cold finger 26, by an electric heating element 37 within chamber 25, by an electric heating element outside of chamber 25, or by a heating element (such as a thin film heater deposited on a cold finger surface) or by any other desired means.

For example, condensed sample gas 27 may be warmed simply by discontinuing the flow of cryogenic fluid through cold finger 26. The flow of cryogenic fluid through cold finger 26 may be varied, such as by momentarily discontinuing such flow, in a manner that regulates the temperature of condensed sample gas 27. One consideration is the need to keep temperatures on all surfaces inside the test chamber substantially uniform.

A cryogenic temperature sensor 36, such as a thermistor or a thermocouple, may be used to monitor the temperature within chamber 25. The temperature sensor can be inside of the cold finger. For example, the temperature sensor can be integrated with the cold finger.

Figure 3:
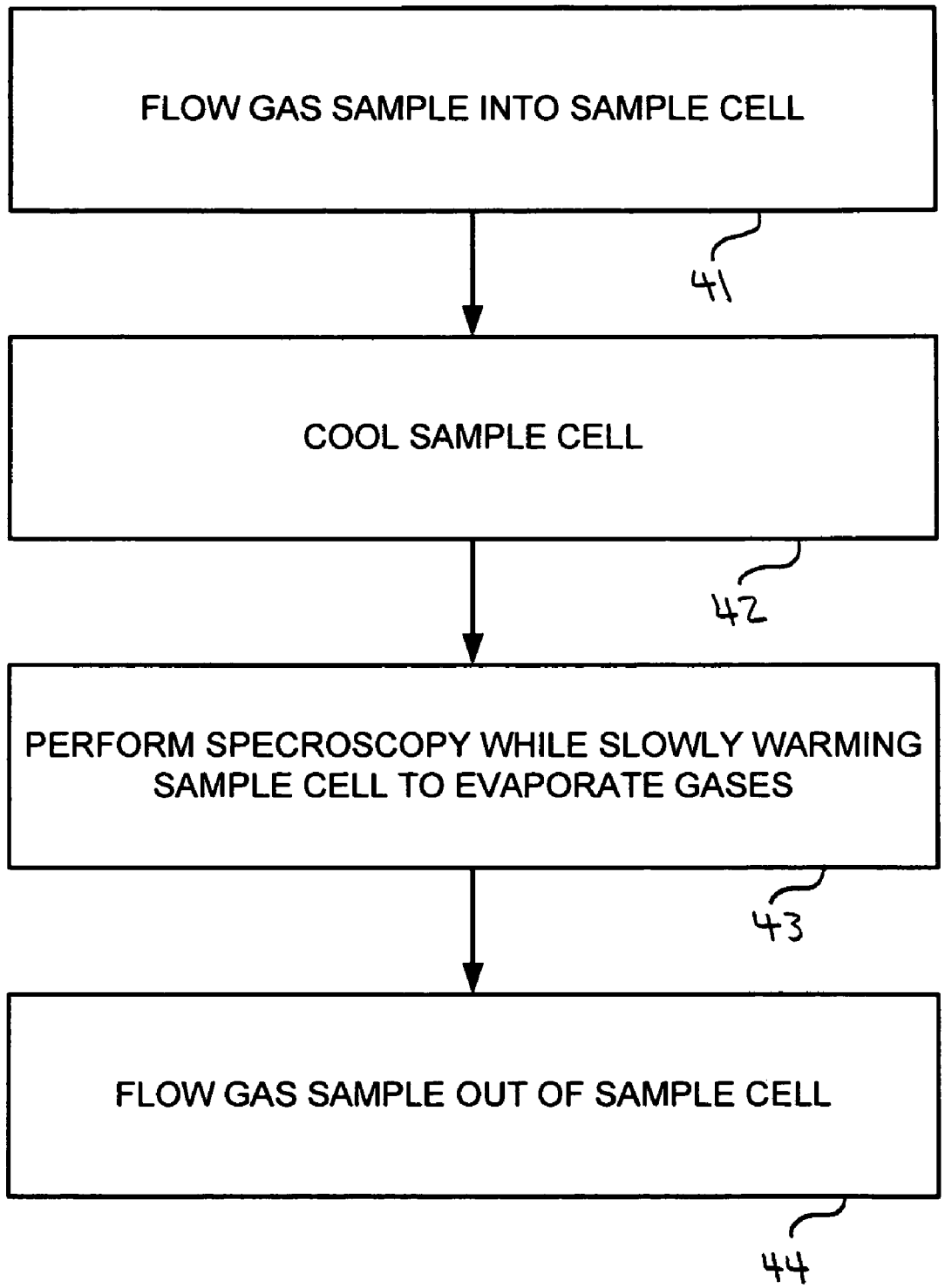
FIG. 3 shows a flow chart illustrating a method for cryogenic terahertz spectroscopy in accordance with an exemplary embodiment of the present invention.

Referring now to FIG. 3, a method for performing cryogenic terahertz spectroscopy may comprise causing a gas sample to flow into a sample cell, as indicated in block 41. The sample cell is then cooled so as to cause the sample gas to condense, as indicated in block 42. As the sample gas is slowly warmed, such that components thereof boil off or evaporate at different times (and at different temperatures), absorption spectroscopy is performed repeatedly as indicated in block 43. The sample gas may then be caused to flow out of the sample cell, as indicated in block 44. The sample cell may then be purged such that it is ready for the introduction of a new gas sample.

Procedures may be implemented to prevent liquefied and/or frozen gas of the gas sample from undesirably, e.g., prematurely, evaporating due to reduced pressure in the sample cell. For example, the sample cell may be sufficiently cooled so as to mitigate such undesirable evaporation and/or the pressure within the sample cell may be maintained at a level that mitigates such undesirable evaporation. One way of maintaining pressure within the cell is by adding an inert gas thereto.

Figure 4:
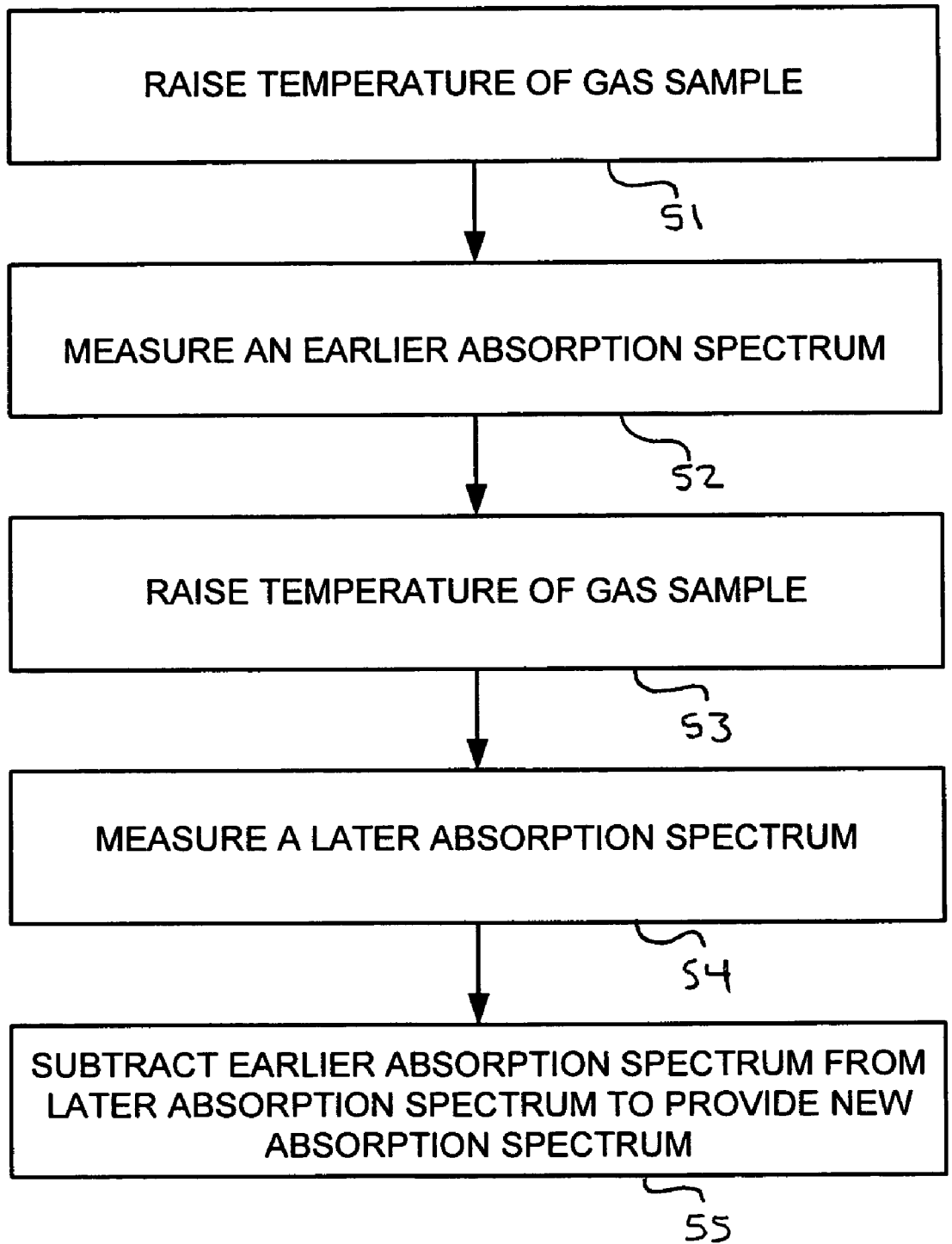
FIG. 4 shows a flow chart illustrating the performance of spectroscopy while warming the sample cell in further detail.

Referring now to FIG. 4, the method of performing absorption spectroscopy of FIG. 3 is shown in further detail. The temperature of the gas sample is raised to a desired temperature, as indicated in block 51. The temperature of the gas sample may be raised by raising the temperature of the walls of the sample cell, a portion of the sample cell, surface of a cold finger, or the like. The temperature may be raised by a discrete, predetermined increment, Δt, as discussed above.

Alternatively, the temperature may be raised by any other desired amount. For example, an operator may choose to raise the temperature by a different amount based upon experience. As a further example, automated control equipment may raise the temperature a different amount based upon results of prior analyses, e.g., prior absorption spectra, or based upon any other criteria.

A first or earlier absorption spectra of the gas sample is measured, as indicated in block 52. Next, the temperature is again raised, either by a fixed amount Δt, or by any other desired amount, as indicated in block 53. Then a second or later absorption spectra of the gas sample is measured, as indicated in block 54.

When two consecutive (or non-consecutive) absorption measurements have been made, then the earlier, e.g., first absorption spectrum may be subtracted from the later, e.g., second, absorption spectrum to define a new absorption spectrum, as indicated in block 55. The new absorption spectrum contains information relating to the sample gas components that boiled off at the new temperature. The process of raising the temperature of the gas sample, measuring the absorption spectrum, and determining a new absorption spectrum using two previously performed absorption spectra is repeated across the desired temperature range.

In this manner, the terahertz absorption spectrum of a complex gas sample may be divided into a plurality of separate absorption spectra. Each of the divided absorption spectra may be substantially simpler (have fewer absorption bands) than a composite absorption spectrum taken without such varying of the temperature of the sample gas.

One or more embodiments of the cryogenic terahertz spectroscopy method of the present invention may be used in a variety of different applications. For example, the present invention may be used to identify hazardous, toxic, or dangerous gases in the air. Applications include the battlefield detection of poisonous gases, use in mines to detect deadly gases, and use in laboratory analysis.

By performing a series of separate absorption spectroscopic measurements upon a corresponding series of separate components or groups of components of a sample gas, the resulting spectra are likewise separated. Because the spectra are separated, the resolution requirements of the spectroscopy system are reduced. Each individual absorption spectrum is substantially less complicated.

This inherently reduces the resolution necessary to distinguish absorption bands. Thus, a Time Domain Terahertz Spectroscopy (TDTS) system may use terahertz radiation sources and detectors having reduced resolution capabilities. Since the resolution requirements are mitigated, less expensive and more readily available terahertz sources and detectors may be used.

Although embodiments of the present invention are described as being used in terahertz frequency domain, the present invention may be used in other bands of the electromagnetic spectrum (millimeter waves, sub millimeter waves, infrared, even in the visible wavelength range), as well as in other types of chemical analysis. As such, description of the present invention as being used in terahertz spectroscopy is by way of example only, and not by way of limitation.

The terms evaporate, vaporize, and boil may be used interchangeably herein and may refer to sublimation. The frozen or condensed sample gas may be either a solid, a liquid, or some combination thereof. In any instance, the terms evaporate, vaporize, and boil may refer to the condensed sample gas becoming gaseous.

Embodiments described above illustrate but do not limit the invention. It should also be understood that numerous modifications and variations are possible in accordance with the principles of the present invention. Accordingly, the scope of the invention is defined only by the following claims.

We claim:

1. A sample cell for use in spectroscopy, comprising:
   a sample chamber; and
   a condensation surface disposed within the sample chamber,
   wherein the condensation surface is configured such that gas condenses thereon when the sample cell is cooled and gas evaporates therefrom when the sample cell is warmed, and
   the sample cell is configured for cryogenic cooling and warming of gas within the sample chamber in discrete temperature steps to cause component gases of the gas to evaporate at different times.

2. The sample cell as recited in claim 1, wherein at least one cryogenic cooling conduit facilitates cooling thereof.

3. The sample cell as recited in claim 1, wherein at least one cryogenic cooling conduit disposed within the sample cell facilitates cooling thereof.

4. The sample cell as recited in claim 1, wherein at least one cryogenic cooling conduit disposed outside of the sample cell facilitates cooling thereof.

5. The sample cell as recited in claim 1, further comprising:
   a gas inlet port for communicating gas to the sample chamber;
   a gas outlet port for communicating gas from the sample chamber;
   a terahertz radiation input window for transmitting terahertz radiation to the sample chamber;
   a terahertz radiation output window for transmitting terahertz radiation out of the sample chamber; and
   at least one cryogenic cooling conduit configured to facilitate cooling of the gas.

6. The sample cell as recited in claim 1, further comprising:
   a least one reflector configured so as to reflect terahertz radiation within the chamber.

7. The sample cell as recited in claim 1, further comprising;
   a plurality of reflectors configured so as to increase a path length of terahertz radiation within the sample chamber.

8. A terahertz spedroscopy system comprising:
   source of terahertz radiation:
   a detector of terahertz radiation;
   source of sample gas;
   sample cell configured to:
      receive the sample gas:
      receive terahertz radiation from the source of terahertz radiation;
   transmit the terahertz radiation to the detector after the terahertz radiation has passed through the sample gas; and facilitate cryogenic cooling and warming of the sample cell in discrete temperature steps to cause component gases of a sample gas within the sample cell to evaporate at different times.

9. The terahertz spectroscopy as recited in claim 8, wherein a cryogenic cooling structure facilitates cooling of gases in the sample cell.

10. The terahertz spectroscopy as recited in claim 8, wherein the sample cell comprises:
   a sample chamber;
   a gas inlet port for communicating gas to the sample chamber;
   a gas outlet port for communicating the gas from the sample chamber;
   a terahertz radiation input window for transmitting terahertz radiation to the sample chamber;
   a terahertz radiation output window for transmitting terahertz radiation out of the sample chamber; and
   at least one cryogenic cooling structure configured to facilitate cooling of the gas.

11. The terahertz spectroscopy as recited in claim 8, wherein the sample cell comprises:
   a sample chamber;
   a condensation surface disposed within the sample chamber; and
   wherein the condensation surface is configured such that gas condenses thereon when the sample cell is cooled and gas evaporates therefrom when the sample cell is warmed.

12. The terahertz spectroscopy as recited in claim 8, wherein the sample cell comprises;
   a sample chamber; and
   a least one reflector configured so as to reflect terahertz radiation within the chamber.

13. The terahertz spectroscopy as recited in claim 8, wherein the sample cell comprises:
   a sample chamber; and
   a plurality of reflectors configured so as to increase a path length of terahertz radiation within the sample chamber.

14. The terahertz spectroscopy as recited in claim 8, wherein the source of terahertz radiation comprises a variable frequency source of terahertz radiation.

15. method of performing spectroscopy, the method comprising:
   flowing sample gas into a sample cell;
   cooling the sample cell so as to condense the sampling gas;
   warming the sample gas in discrete temperature steps as to cause component gases of the sample gas to evaporate at different times; and
   performing spectroscopy upon the component gases.

16. The method as recited in claim 15, wherein cooling the sample cell comprises flowing a cryogenic fluid through a conduit of the sample cell.

17. The method as recited in claim 15, wherein warming the sample cell comprises warming the sample cell at a rate that is consistent with the desired spectroscopic resolution.

18. The method as recited in claim 15, wherein performing spectroscopy upon the component gases comprises transmitting terahertz radiation into the sample cell, the terahertz radiation being scanned through a frequency range.

19. The method as recited in claim 15, wherein
   performing spectroscopy upon the component gases comprises defining a series of absorption spectra as different gasses evaporate.

20. The method as recited in claim 15, wherein performing spectroscopy upon the component gases comprises:
   defining a first absorption spectra;
   from the second is consistent with the desired spectroscopic resolution absorption spectrum to define a third absorption spectrum.

21. The method as recited in claim 15, wherein warming the sample cell and performing spectroscopy is performed to perform spectroscopy upon a plurality of gas components having successively higher boiling points.

22. The method as recited in claim 15, wherein performing spectroscopy comprises applying terahertz radiation using a plurality of separate sources thereof.

23. The method as recited in claim 15, further comprising digitally recording each absorption spectrum.

24. The method as recited in claim 15, further comprising analyzing an absorption spectrum so as to determine components of the gas sample.

25. The method as recited in claim 15, wherein performing spectxoscopy comprises varying a terahertz source continuously so as to facilitate measurement of an absorption spectra.

26. The method as recited in claim 15 further comprising removing the sample gas from the sample cell after performing spectroscopy and flowing new sample gas into the sample cell and performing another sequence of spectroscopic measurements upon the new sample gas.

* * * * *